(12) United States Patent
Saaski

(10) Patent No.: US 10,318,845 B2
(45) Date of Patent: Jun. 11, 2019

(54) COUPON READER

(71) Applicant: RESEARCH INTERNATIONAL, INC., Monroe, WA (US)

(72) Inventor: Elric Saaski, Monroe, WA (US)

(73) Assignee: RESEARCH INTERNATIONAL, INC., Monroe, WA (US)

( * ) Notice: Subject to any disclaimer, the term of this patent is extended or adjusted under 35 U.S.C. 154(b) by 0 days.

(21) Appl. No.: 16/158,221

(22) Filed: Oct. 11, 2018

(65) Prior Publication Data

US 2019/0042877 A1 Feb. 7, 2019

Related U.S. Application Data

(63) Continuation-in-part of application No. 15/487,397, filed on Apr. 13, 2017, now Pat. No. 10,192,144.
(Continued)

(51) Int. Cl.
*G06K 9/62* (2006.01)
*G06T 7/90* (2017.01)
(Continued)

(52) U.S. Cl.
CPC .......... *G06K 9/6215* (2013.01); *G01N 21/78* (2013.01); *G06K 9/6202* (2013.01); *G06T 7/90* (2017.01);
(Continued)

(58) Field of Classification Search
None
See application file for complete search history.

(56) References Cited

U.S. PATENT DOCUMENTS 6,639,663 B1 10/2003 Markle
8,131,477 B2 3/2012 Li et al.
(Continued)

FOREIGN PATENT DOCUMENTS

| CN | 104777159 A | * | 7/2015 |
| EP | 2313787 B1 | | 11/2017 |
| WO | 2010021873 A3 | | 1/2010 |

OTHER PUBLICATIONS

Machine Translation of CN 104777159 A (Year: 2015).*
(Continued)

*Primary Examiner* — Michelle M Entezari
(74) *Attorney, Agent, or Firm* — Timothy E. Siegel Patent Law, PLLC; Timothy E. Siegel

(57) ABSTRACT

A method of reading a coupon channel that displays a test section pattern after being exposed to a target substance, the method uses a device having a computer readable memory, digital camera, logic assembly and user interface; providing a pixel target intensity profile; placing the coupon in the device and exposing the coupon channel to a test fluid mixture; automatically using the digital camera to take a digital image of the coupon channel test section after the exposure. The improvement in the method includes finding the contiguous set of pixels from the test section of the coupon channel that best matches the intensity profile of the target pattern representation and determining if this best match set of pixels exceeds a similarity threshold and in response to a best match set of pixels passing the similarity threshold, automatically providing a human perceptible indication that the target substance has been detected.

6 Claims, 5 Drawing Sheets

Related U.S. Application Data

(60) Provisional application No. 62/322,357, filed on Apr. 14, 2016.

(51) Int. Cl.
  *G06T 7/00* (2017.01)
  *G01N 21/78* (2006.01)
  *G01N 21/77* (2006.01)
  *H04N 5/232* (2006.01)

(52) U.S. Cl.
  CPC .............. *G01N 2021/7756* (2013.01); *G01N 2201/125* (2013.01); *G06T 7/0014* (2013.01); *G06T 2207/10024* (2013.01); *G06T 2207/30072* (2013.01); *H04N 5/232* (2013.01)

(56) References Cited

U.S. PATENT DOCUMENTS

| | | | |
|---|---|---|---|
| 8,194,170 B2 | 6/2012 | Golub | |
| 8,411,916 B2 | 4/2013 | Hsieh et al. | |
| 8,583,379 B2 | 11/2013 | Li et al. | |
| 8,698,881 B2 | 4/2014 | Fleming et al. | |
| 8,824,800 B2 | 9/2014 | Bremnes et al. | |
| 8,865,089 B2 | 10/2014 | Blatt et al. | |
| 8,889,424 B2 | 11/2014 | Ehrenkranz et al. | |
| 8,916,390 B2 | 12/2014 | Ozcan et al. | |
| 9,241,663 B2 | 1/2016 | Jena et al. | |
| 9,386,221 B2 | 7/2016 | Kauniskangas et al. | |
| 9,390,237 B2 | 7/2016 | Myers et al. | |
| 9,600,878 B2 | 3/2017 | Tsai et al. | |
| 2002/0155617 A1 | 10/2002 | Pham | |
| 2005/0114332 A1* | 5/2005 | Lee | G06K 9/6857 |
| 2007/0108284 A1 | 5/2007 | Pankow | |
| 2007/0268720 A1 | 11/2007 | Rowe | |
| 2008/0304723 A1 | 12/2008 | Hsieh et al. | |
| 2010/0015611 A1* | 1/2010 | Webster | G01N 21/6428 435/6.18 |
| 2012/0189171 A1 | 7/2012 | Abiko | |
| 2013/0280698 A1 | 10/2013 | Propper et al. | |
| 2014/0065647 A1 | 3/2014 | Momenta | |
| 2015/0056719 A1 | 2/2015 | Karlovac et al. | |
| 2015/0100279 A1 | 4/2015 | Ronnekleiv | |
| 2015/0336511 A1* | 11/2015 | Ukeda | B60R 1/00 348/148 |
| 2016/0080548 A1 | 3/2016 | Erickson et al. | |
| 2016/0131592 A1 | 5/2016 | Cooper | |
| 2017/0300779 A1 | 10/2017 | Saaski et al. | |

OTHER PUBLICATIONS

Nowak, S. H., Bjeoumikhov, A., von Borany, J., Buchriegler, J., Munnik, F., Petric, M., . . . & Wedell, R. (2015). Sub-pixel resolution with a color X-ray camera. Journal of Analytical Atomic Spectrometry, 30(9), 1890-1897. (Year: 2015).*

Genprime D-Cipher-151229, http://www.genprime.com/doa-test-reader.

Guardian Reader Manual, Alexeter Technologies, LLC, Wheeling, IL.

NIDS® Stand-Alone Reader III User Manual, Smiths Detection, Inc., Danbury, CT.

Tetracore Biothreat Alert Reader; http://www.tetracore.com/bio-warfare/index.html.

\* cited by examiner

COUPON READER

RELATED APPLICATIONS

This application is a continuation-in-part of U.S. patent application Ser. No. 15/487,397 filed Apr. 13, 2017, which claims the benefit of U.S. Provisional Application No. 62/322,357, filed Apr. 14, 2016, which are both incorporated by reference as if fully set forth herein.

FIELD OF THE INVENTION

The embodiments herein relate to devices and methods for reading a coupon that displays a pattern when a target substance is detected.

BACKGROUND

A "coupon reader" is a device that accepts a "coupon," typically a planar tray having a chemically reactive section that is imbued with a chemical mixture that is designed to react to a target substance and forms a visually detectable indicator pattern after a predetermined development time. A common implementation is the lateral flow immunoassay. The term "ticket" is also sometime used to refer to a coupon. Generally, coupons are designed to be read by a human technician, although coupon readers are also becoming common. The reader automates detection of the indicator pattern, removing reliance on human interpretation. Typically, a single company makes both coupons and the readers for those coupons, but there are also companies that do not make coupons, but do make coupon readers for coupons made by other companies ("third-party coupon readers"). Some coupons have only one section that reacts to a single target substance, whereas other coupons have a number of sections, each one designed to react to a different target substance. Coupons come in various sizes, but it appears that no currently available coupons are greater than 15 cm in any dimension.

Coupons are used to detect substances of interest in the medical and public safety fields. For example, some coupons are designed to accept a bodily fluid onto the chemically reactive sections, to detect a naturally occurring target compound, such as a hormone, or a toxin. A public safety coupon can accept samples from many sources, including aerosolized particulates, liquids, and solids. Air-derived samples, mixed and concentrated into a liquid solution, and placed onto the chemically reactive sections, can provide an indication of an aerosol poison. Typically, the sample is incorporated into a buffer solution that is applied to the coupon, to facilitate the exposure of the coupon chemicals to the atmospheric agent or test specimen. Each chemically reactive section is referred to as a channel. Coupons may have multiple channels, each detecting a different target substance, allowing for multiple assays on a single coupon. Each channel typically includes a control section, which will develop in tandem with the test section of the coupon (the portion of the coupon on which the test line will appear), but unlike the test section will display the indicator pattern, whether or not the target substance is present. The control section performs two functions, first, if the control section does not display the indicator pattern it is generally an indication that something has gone wrong with the process of exposure. Accordingly, a negative reading does not, in that instance, indicate an absence of the target substance, but only indicates a test that was not performed correctly. Also, it shows the test personnel what the indicator pattern looks like.

In many situations, it is important to obtain a quick result from the coupon exposure, but the coupon manufacturer may have designated a set period of time for the indicator pattern to develop. Human technicians may set the coupon aside and attend to other tasks while the coupon develops for the manufacturer-specified time period. Variation in buffer solution and how it is applied can cause the same coupon to develop differently even when exposed to the same concentration of target substance. The use of a reader can lead to a faster detection of the indicator pattern when compared to a human, particularly in low light or stressful situations.

For the purpose of automatically analyzing the visually detectable indicator pattern of the coupon using a camera, it is desirable to provide uniform illumination over the surface of the coupon, as this allows full use of the camera's dynamic range over the entire field of view. As an example, if pixels directly under the light source have a reflected intensity of 255 units while more dimly illuminated pixels at the edge of the coupon have a maximum reflected intensity of 128, then the dynamic range and resolution of a measurement may be lower by a factor of two for assay channels near the coupon edge as compared to channels directly under the light source. In addition, if light rays illuminate a particular part of the coupon surface at oblique angles only, shadows can be created that confound analysis of assay results. These issues are compounded by the fact that a compact portable device is desirable, as it is more easily moved from place to place. Most bioassay coupons are on the order of 11 cm in maximum diagonal measurement, and in the interests of having a compact device, it is desirable that the distance from the coupon to the camera lens is of similar magnitude. To maximize the number of pixels in the analysis, it is also essential that the coupon fill the field of view as much as possible. That is, a near-field macro imaging design is preferred.

Light sources typically used for camera systems are so-called "white LEDs." Uniform near-field illumination is sometimes accomplished using a circular array of white LEDs surrounding the camera lens, referred to as a ring light. Ring lights may have multiple circular rings of LEDs and may contain more than 100 LEDs. Such a large number of LEDs could significantly reduce battery life and thus operation lifetime in a battery-operated instrument. In addition, commercially-available ring lights still produce an illumination field in which intensity peaks in the center and drops off radially, albeit much more gradually than with a single LED. Since bioassay coupons are typically rectangular, ring lights may not provide uniform edge-to-edge illumination.

Using a single LED light source is far preferable, but the hotspot problem must be solved. The LED cannot be mounted on the same axis as the camera lens: It must be physically located to the side of the lens, and the hotspot consequently appears at an off-axis camera image point. This does not improve the situation since parts of the coupon remain farther away than others from the LED, and light intensity over the coupon surface can be significantly non-uniform across the face of the coupon.

Some improvement in light uniformity can be realized if a piece of ground glass or opalescent glass is mounted directly under the light source. This causes light to be re-emitted in a Lambertian pattern by virtue of the ground glass's surface roughness or by internal refraction in the opalescent glass. That is, the distribution of light emerging from the surface approximates a cosine function relative to a surface normal. These methods more broadly disperse the light, but there still remains a radial distribution of ever-decreasing light intensity relative to an axis passing through the LED source's center point and perpendicular to its surface.

Therefore, there remains a need in the art for improved methods of reading a coupon that, among other things, minimize or compensate for variations in illumination over the surface of the coupon.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a method of reading a coupon channel that displays a test pattern in a test section after being exposed to a target substance, the method includes providing a device having a computer readable memory, a digital camera, a logic assembly and a user interface; providing a color-ratio pixel target pattern representation, representative of an exposed and at least partially developed coupon channel control section pattern; placing the color-ratio pixel target pattern into the memory; placing the coupon in the device and exposing the coupon channel to a test fluid mixture; automatically using the digital camera to take a digital image of the coupon channel test section after the exposure, the digital image formed of color pixels, each containing at least two sub-pixels representing the intensity of two different colors. The improvement in the method includes for each color pixel forming a color-ratio pixel by forming the ratio of a first one of the two subpixels with the other, and automatically using the logic assembly to compare the color-ratio pixels in the test section as shown in the digital image to the color-ratio pixel target pattern representation to determine if the test section passes a similarity threshold; and in response to a test section passing the similarity threshold, automatically providing a human perceptible indication that the target substance has been detected.

In a second separate aspect, the present invention may take the form of a method of reading a coupon channel that displays a test section pattern after being exposed to a target substance, the method uses a device having a computer readable memory, digital camera, logic assembly and user interface; providing a pixel target intensity profile; placing the coupon in the device and exposing the coupon channel to a test fluid mixture; automatically using the digital camera to take a digital image of the coupon channel test section after the exposure. The improvement in the method includes finding the contiguous set of pixels from the test section of the coupon channel that best matches the intensity profile of the target pattern representation and determining if this best match set of pixels exceeds a similarity threshold and in response to a best match set of pixels passing the similarity threshold, automatically providing a human perceptible indication that the target substance has been detected.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION

Figure 1:
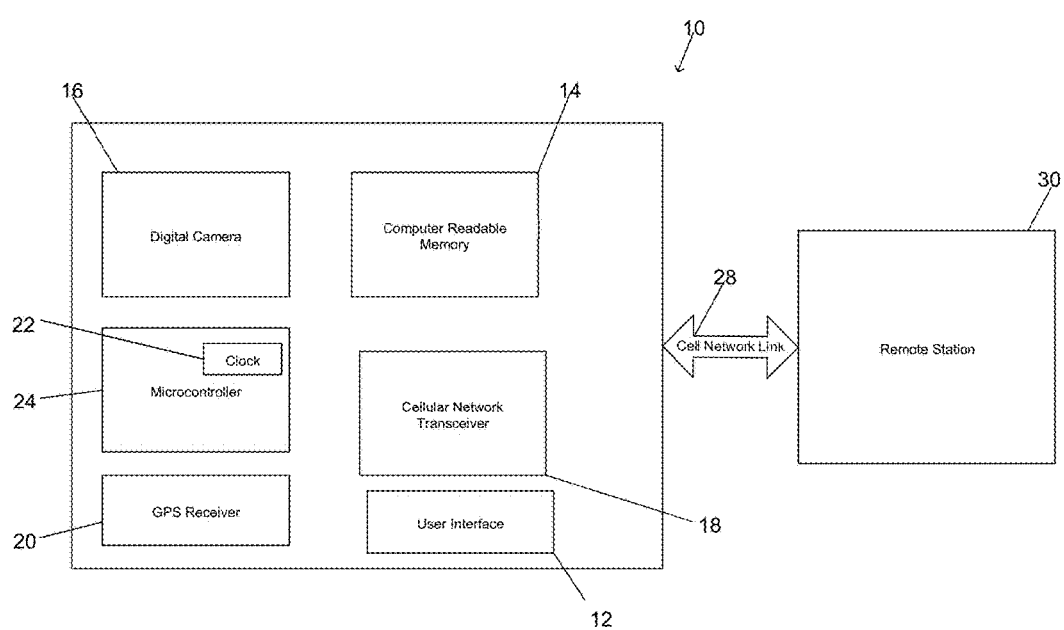
FIG. 1 is a block diagram of a preferred embodiment.

Referring to FIG. 1, which is a block diagram of a preferred embodiment, in one preferred embodiment a coupon reader 10 includes a generally tight light chamber (see FIG. 3, as defined by walls 38) which is adapted to permit the introduction of any currently commercially available coupon (anything that is smaller than a 15 cm×10 cm×1 cm cuboid). The reader 10 includes a user interface 12 that prompts a user to enter the type of coupon being introduced into reader 10. In one embodiment interface 12 includes a liquid crystal display coupled with a few keys (not shown), for making a choice of options presented on the display, and for providing a user perceptible indication. Interface 12 may also include a light or sound indicator for providing the human perceptible indication. In another embodiment, a voice recognition element (not shown) is included. In yet another embodiment, a USB port (not shown) is provided for a keyboard or a computer to be connected for commands and information to be sent to reader 10. A computer readable memory 14 and a microcontroller 24, driven by a clock 22, collectively forms a logic assembly for controlling a digital camera 16 and interpreting digital imagery taken by camera 16, to form a detection, or determine that no detection has occurred. A GPS receiver 20 determines location, which is input to microcontroller 24. The location information together with test results is sent by way of a cellular network transceiver 18 over a cellular network link 28 to a remote station 30, for storage. In one preferred embodiment, remote station 30 includes a mapping feature permitting users to see test results displayed on a map at the locations where the various test results were formed.

In one embodiment, means are provided to introduce a target pattern representation (an image of a developed coupon) into a computer readable memory 14 of reader 10. This data entry may be performed by placing a developed coupon or a control section into reader 10 and using user interface 12 to command reader 10 to use a digital camera 16 to take a digital photograph of the developed coupon and store it in the computer readable memory 14, properly labeled as a digitized image of a target pattern. In another preferred embodiment, reader 10 is provided with digitized target images already stored. Otherwise digitized target images may be introduced into reader 10 by way of the USB port (not shown) or may be downloaded by way of a cellular network transceiver 18.

After an exposed coupon is introduced into reader 10, the microcontroller 24 controls the digital camera 16 to repeatedly form images of each coupon channel and effectively compare each image with the digitized target image stored in computer readable memory 14.

Coupon manufacturers typically identify a specific time period that should elapse between exposing the coupon to the substance to be tested and reading the results on the coupon. In some cases, results may be visible before this predetermined development time has elapsed and time may be wasted by continuing to wait for the entire pre-determined time period. The ability of the coupon reader 10 to determine when an indicator pattern has been detected and to alert any nearby people that detection has occurred helps to eliminate this wasted time. It will be appreciated that this ability is particularly important when the coupon reader is being used to detect the presence of toxic or harmful compounds in a public safety context, where time may be of the essence.

Figure 2:
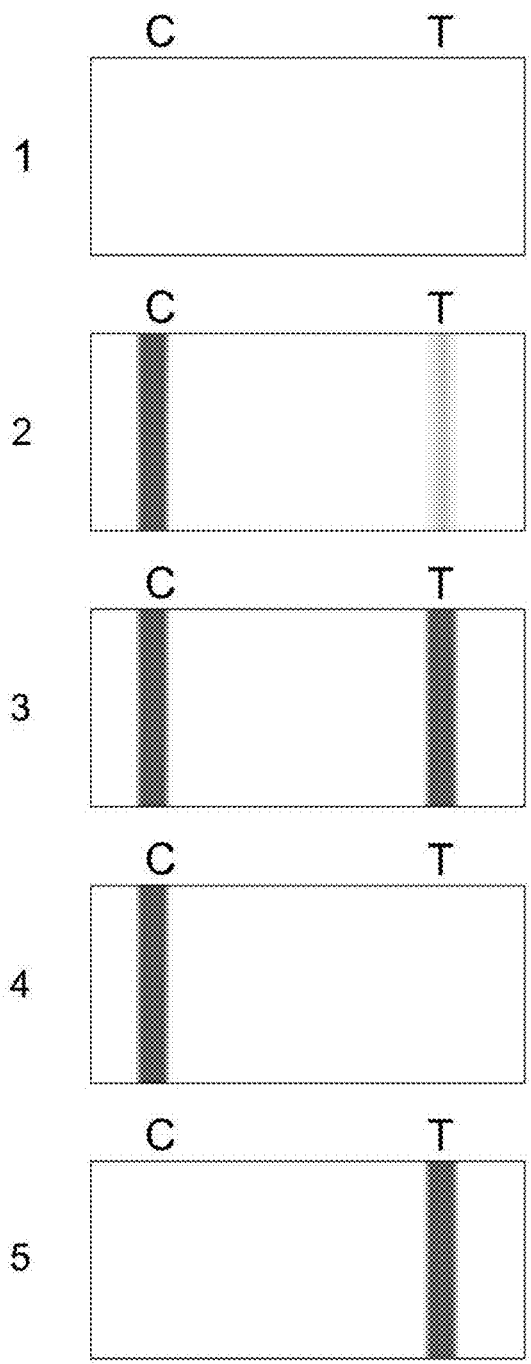
FIG. 2 is an illustration of common exposed coupon channel combinations of test and control pattern indications.

Many other algorithms, including least squares detection and various linear algorithms are used in alternative embodiments. FIG. 2 is an illustration of test patterns that are commonly encountered and which are amenable to interpretation and quantification using the mathematical and algorithmic approaches revealed herein. The left half of the coupon shown would typically be referred to as the "control section" and the right half as the "test-section" where the test line appears.

Prior to channel analysis, all embodiments require that the coupon image is recognized in the digital image being analyzed. Immediately following coupon image capture, image recognition routines analyze the captured image and identify channel locations based on the detection of characteristic coupon features. In embodiments, the user has entered the coupon type, and this information facilitates the recognition of the channel locations. The processing described below relates to each channel analyzed.

Known optical features of the coupon are pre-loaded into the device before use. Image recognition tools identify the coordinates of these characteristic features for each different coupon type. The pixel coordinates of these features provide reference points and allow each coupon image to be overlaid by a coordinate map which can then be used to locate the assay channels.

Upon positive recognition and satisfaction of location criteria, coupon analysis is allowed to continue. Upon detection of an abnormal situation, such as the coupon being inserted 90 or 180 degrees from the correct orientation, the user is alerted to the type of error. Once the error is remedied and location criteria are satisfied, sample analysis procedures may proceed.

In one embodiment, each time a reader 10 processes a coupon, the results are time, position and device code stamped, with position being provided by a GPS reader 20, time being provided by a clock 22, and device being provided by device firmware, all controlled by microcontroller 24 and stored in computer readable memory 14. In a preferred embodiment, this information is uploaded periodically via cell network link 28 using cell network transceiver 18, to a remote station 30. In one embodiment, remote station 30 includes a display and may be commanded to display a map of an area, showing the locations, times, results and device codes of each coupon reading.

Referring to FIG. 2, a coupon channel is shown at different end results of exposure. illustration 1 shows a coupon channel in which neither test line T nor control line C developed. This could indicate an unused coupon channel but could also indicate a coupon channel that has not been properly exposed to buffer solution. The absence of a control pattern indication, in this instance, prevents a false conclusion that the target substance is not present. Illustration 2 is a weak positive indication, due to the weak pattern. Illustration 3 is a strong positive, whereas illustration 4 shows an absence of the target substance. Illustration 5 indicates that something has gone wrong with the test, as the control line should always develop, especially if the test line appears.

Figure 3:
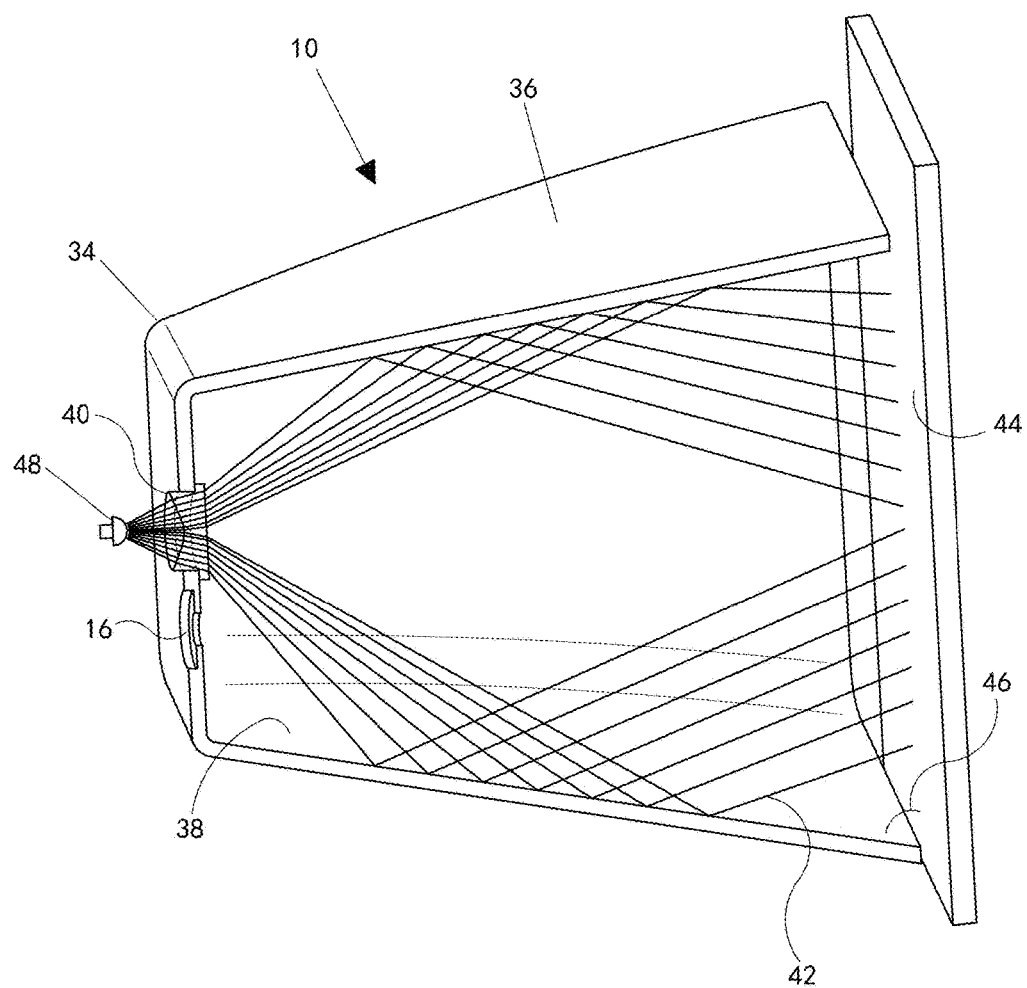
FIG. 3 is a cross section of an apparatus for reading coupons according to one preferred embodiment, showing the position of the coupon relative to the apparatus and the path taken by light passing through the negative axicon lens.

Referring now to FIG. 3, which is a cross section of an apparatus for illuminating and capturing coupon images, in one preferred embodiment the coupon reader 10 includes a light diffusing assembly 34 comprising side walls 36 having reflective interior surfaces 38 and a negative axicon lens 40. The negative axicon lens 40 alters the path of light rays 42 emitted from light source 48 and passing thought the lens such that the light rays 42 reflect off the interior surfaces 38 prior to reaching the coupon surface 44. The negative axicon lens 40 is designed to prevent any light from directly impinging on the coupon surface 44. All LED output light is first operated on by the light diffusing assembly 34 before it impinges on the coupon. An optimum shape for the light diffusing assembly 34 is empirically determined, but it has been found that for illuminating a rectangular coupon, a concave structure that has a rectangular cross-section works well if the lower skirt of the structure approximates the coupon's outer shape.

In one embodiment, the light diffusing assembly comprises side walls 36 which form a rectangular cross-section approximately 8 cm on a side. The side walls 36 meet the coupon surface 44 at angles that maximize uniformity of illumination over the coupon surface and compensate for the light source's off-center location. In a preferred embodiment, the included angle 46 between the side walls 36 and the coupon surface 44 is:

Face 1=70 degrees
Face 2=70 degrees
Face 3=70 degrees
Face 4=70 degrees

In one embodiment, the distance between the coupon surface 44 and the negative axicon lens 40 is 15 cm.

Diffuse reflection may be obtained from the reflective interior surfaces 38 by covering them with a flat or gloss white paint, or by constructing the structure using a white polymer. However, commercially available white polymers may absorb a significant amount of the optical power impinging on them, and this may need to be taken into consideration.

Optionally, the reflective interior surfaces 38 may be covered with a colored coating rather than a white coating. A colored coating may be desirable in circumstances where a specific light spectrum distribution is preferred for illuminating certain types of coupon. In a further option, the reflective interior surfaces may be covered by a hybrid coating that provides a mixture of specular and diffuse reflection.

Axicons are special lenses that have at least one active surface that is conic in shape. They will typically take a point source of light and transform it into either a line or circle of light. A negative axicon lens is used for coupon reader 10. Typical commercially available axicon lenses are designed to form a specific geometric shape, and for that reason are considered "positive axicons." The negative axicon, in contrast, takes a point of light and transforms it into an annular fan of light. Instead of a centrally located solid cone of material as in a positive axicon, the negative axicon has a conic pocket into which source light expands.

Refraction at the conic top surface and at the optionally planar lower surface cause rays from a point source to be distributed over a range of angles determined by the conic profile, the distance of the source from the lens, the lens thickness, and the refractive index of the lens material. Angular emission of the lens can be tuned so that no light hits the coupon surface 44 without first reflecting off the reflective interior surfaces 38. That is, in a preferred embodiment, no light passing through the negative axicon lens 40 falls directly on the coupon surface 44, particularly at the spot immediately below the lens where a hotspot would normally occur. In this way, all light impinging on the coupon surface 44 is diffused light re-emitted or reflected by the reflective interior surfaces 38 and the uniformity of illumination over the coupon is greatly improved, even if the coupon is in close proximity to the light source and lens.

It is not necessary that the conic profile of the negative axicon lens 40 be a simple cone. By adjusting the surface profile of the lens, the distribution of emitted optical power can be modified in an angular sense. Since the objective of the negative axicon lens and light diffusing assembly is to provide diffused illumination, minor errors in the surface profiles are not critical. In one embodiment, the lenses are manufactured on a CNC lathe, followed by vapor polishing to remove macroscopic tooling marks.

In one embodiment, a negative axicon lens with planar output surface for supplying optical power to the reflective interior surfaces is constructed of clear polycarbonate. In one embodiment, the negative axicon lens has the following dimensions: the overall height of the lens may be 3.5 mm, the diameter may be 10 mm, and the maximum depth of the cone may be 2.5 mm.

In one embodiment, the cone profile is described as:

$$\text{Radius} = 1.98543z - 0.18142z^2 + 0.04361z^3 \text{ (where } z \text{ is the distance in mm from the cone's vertex).}$$

In one embodiment, nonuniformity of illumination across the coupon surface is compensated for by color-based ratiometric analysis of pixel data. Most color cameras provide at least three color sub-pixels per color pixel; typically red, green, and blue sub-pixels. It has been found that light intensity variations over a coupon due to geometric lighting issues are very similar in the three color sub-pixels. Most lateral flow immunoassay coupons use colloidal gold as the line colorant and its peak absorption is typically in the wavelength range of 540 nm to 580 nm, which is principally apparent in the camera pixels sensitive to green and red. It has been discovered that by using the color pixels to form "ratiometric" or, termed slightly differently, "color-ratio" pixels, that is a pixel having an intensity corresponding to the ratio of two sub-pixels, an unexpected and remarkable reduction in background nonuniformity is seen. For the coupons having the common colloidal gold colorant, the red and green sub-pixels are typically most useful in this regard, but creating color-ratio pixels using other color sub-pixels may be preferred for other colorants.

Figure 4:
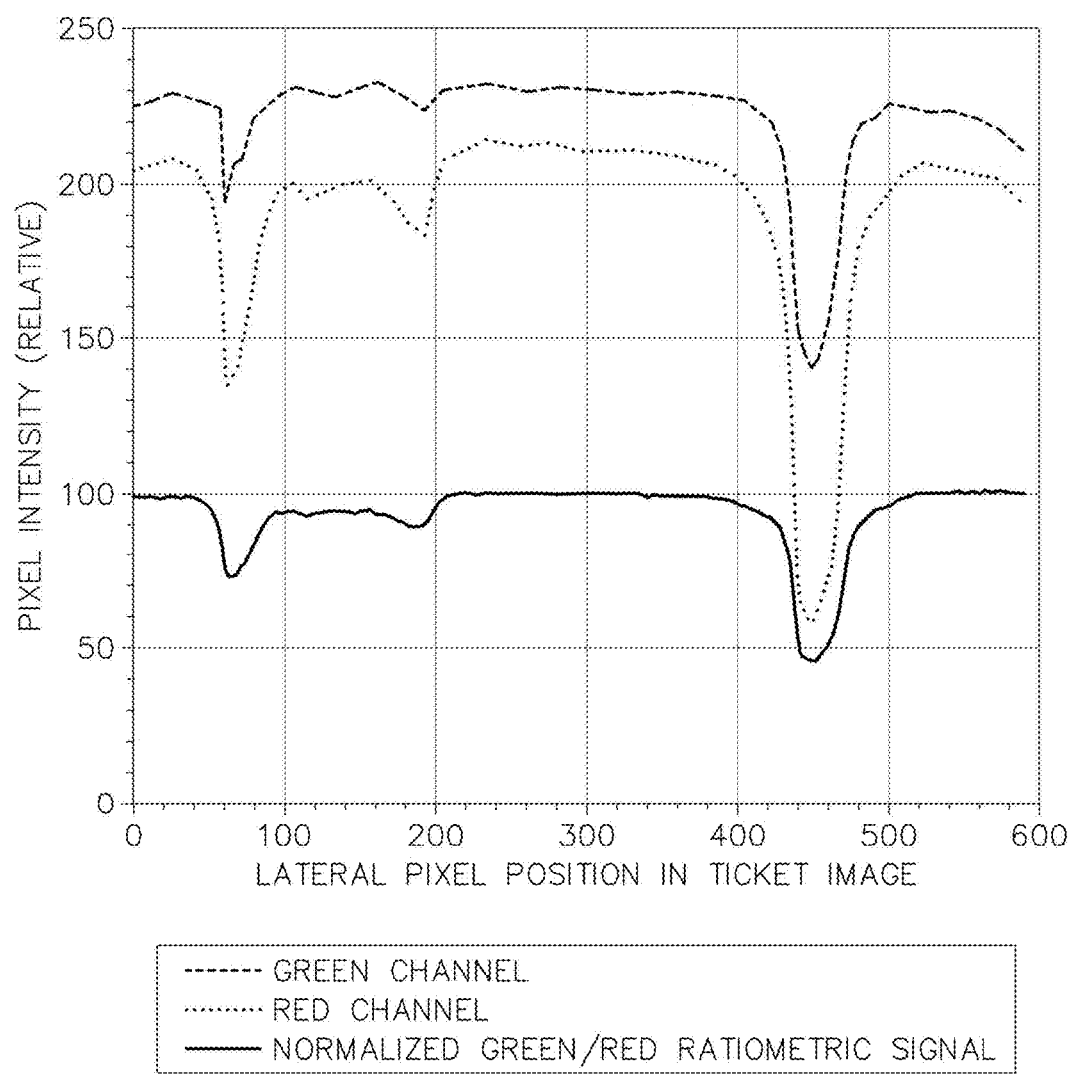
FIG. 4 is a graph showing the elimination of light intensity effects in a developed coupon pattern due to defining a ratiometric signal variable.

FIG. 4 shows raw intensity data for the green and red, column-summed sub-pixels of a coupon channel imaged using a solid state white light flash illuminator. Also shown are the column-summed normalized column-summed green-to-red color-ratio pixel values, forming an "intensity profile." This coupon had previously been exposed to a liquid containing the target substance, and hence displayed the target pattern indicating a positive result. In this case, the target pattern constituted a line having both red and green color components running the width of the channel. The coupon was imaged and the image pixels were divided into columns running parallel to the colorimetric lines. The values of the pixels in each column were summed to create the pixel data sets shown. The large signal perturbation on the left side of FIG. 4 exhibits the two absorbance maxima at approximate pixel locations 65 and 185, respectively, due to colorimetric reactions on the test strip. The pixel signal minimum (with maximum divergence from the mean value) on the right, between pixel positions 400 and 500 is due to the control line and should always be present if the coupon is working properly. Note that there are significant intensity fluctuations in the baselines of both the red and green data sets.

In one embodiment, a new variable is created when the green pixel intensities are divided by the corresponding red pixel intensities, to create green-to-red color-ratio pixels and the resultant curve is normalized to an arbitrary value of 1.0 (or 100%) at some arbitrary pixel location distant from the test and control lines. The resulting color-ratio pixel values are also shown in FIG. 4, normalized to a value of 100. Note the removal of spurious non-signal fluctuations seen in the green and red pixel backgrounds in sections away from the three absorbance maxima, caused by variations in the background light level. This allows the test and control lines to show up much more clearly as deviations from a near-constant color-ratio pixel background signal.

The fluid dynamic and chemical processes that create the test and control lines are typically identical or very similar. For most coupons, even those with multiple identification channels, all test and control lines produce pixel signal responses that are similar in shape and substantively differ only in overall intensity. Therefore, the relative concentration of a targeted material may be estimated by simply comparing the maximum deviation of the color-ratio pixel signal from background and comparing it to the maximum deviation of the fully-formed color-ratio pixel control line. However, this may not be the most suitable method for test lines that have a small peak intensity because there may be too high of a signal-to-noise ratio to determine the peak value accurately. In addition, the test and target lines are of finite width and vary in intensity over the line's width. Therefore, the quantity of target material in the sample is more appropriately proportional to the integrated total response over the entire line width. Using the integrated response over the entire line width will also serve to smooth out pixel signal noise. For example, if a signal is averaged over 100 pixels, random background noise as a fraction of the mean signal value will typically be reduced by a factor of 10 times compared to the noise associated with a single pixel measurement process.

In one embodiment, the following mathematical strategy and corresponding algorithm automatically provide a measure of the test and control line integrated areas, and the degree of match between the shapes or "intensity profiles" of the two lines. This technique yields the pixel (or stated slightly differently, "coupon") location of the test section intensity profile that best matches the reference pattern. That is, the set of contiguous pixels in the test section having an intensity profile that most closely matches that of the reference pattern. The control and test line locations may indicate whether the assay coupon was correctly assembled or not, or if it was subsequently mishandled by the user.

The coupon typically includes a control line, which develops even in the absence of the target substance to indicate that the coupon is functioning properly and that the correct procedures were used to expose and develop the coupon. In one embodiment, the control line is used as the source of reference information that permits the coupon reader to determine whether a test line is present or absent. In other embodiments, a different source of reference information may be used, such as a pre-printed line on the coupon, data from a different coupon, or an abstract representation of a developed control line, showing the expected result when the tested for substance is present.

Figure 5:
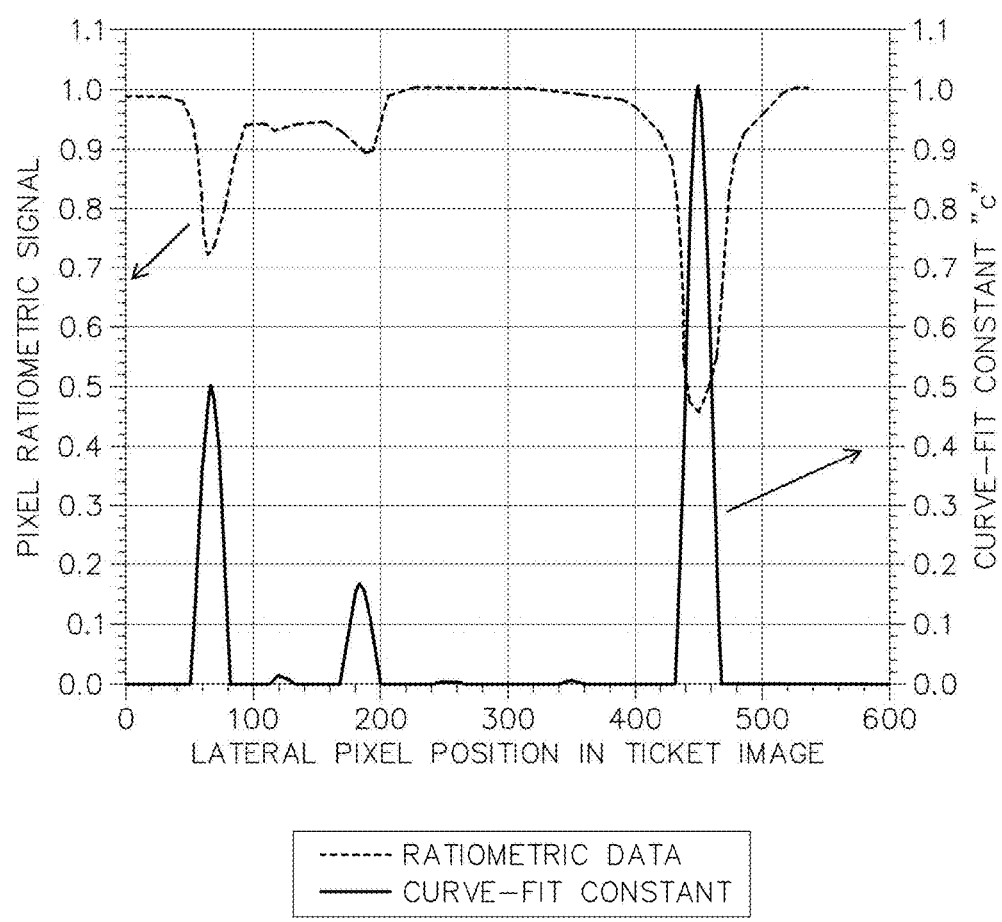
FIG. 5 is a graph showing the application of least-squares nonlinear correlation to identify line strength and pixel location in a developed coupon pattern.

Referring to FIG. 5, because the test and control lines extend across the width of each coupon channel, the color-ratio pixels are divided into columns running parallel to the test and control lines and then summed across each column. Each column sum defined in this way is identified by pixel position and referred to as a "pixel", and the value of the sum at that position is termed the "pixel value" for that position. The color-ratio pixel signal values associated with a coupon's test and control lines can be approximated as the sum of a slowly varying background signal and a characteristically-shaped nonlinear absorbance signature, Y*(i), where "i" is pixel position. The contiguous set of color-ratio pixels between two pixel-positions q and r (where r−q=m), that encompass the control line, for example the 40 pixels between pixel positions 430 and 470 in FIGS. 4 and 5, is such a characteristic control line signature Y*(i). In one embodiment, a two-variable nonlinear least squares regression technique may be used to test for the presence of signal or "test" lines with absorbance signatures similar to Y*(i). This is done by comparing color-ratio pixel test section data, Y(i), to a fitting equation, $Y_f(i)$, which is given as $$Y_f(i) = a + b \times i + c \times Y^*(i)$$

In this equation, "a" is the average baseline value, "b" is the rate of baseline change per pixel, and "c(p)" is a measure of the goodness-of-fit of experimental data over a set of pixels of equal width to the reference signature, Y*(i), and starting at pixel index "p". As noted, in the example of FIG. 5, this set has about 40 scalar values, each representing a column sum of color-ratio pixels, that collectively form the control line. To obtain an unbiased measure of this goodness-of-fit, we minimize the sum of squares of the deviations between the experimental data (that is, the intensity profile of each set of contiguous m pixels in the test section) and the curve fit, $Y_f(i)$, $$\eta = \Sigma_{i=p}^{p+m} [Y(i) - Y_f(i-p)]^2$$

Where p=the starting pixel position and m (as noted above) is the number of values in the Y*(i) set of values and i=0, is the starting pixel position of $Y_f(i)$. The values of a(p), b(p) and c(p) yielding the minimum value of η are found (in the manner described below) repeatedly, for each value of "p" over the test section of the coupon. In the example of FIG. 4, the values of c(p) are shown for every value of p, from p=1 to p=600, but this is done to show that the least squares fit of Y*(i) with itself yields a c(p) of 1. To determine whether a target substance has been found, it would be more typical to find the values of c(p) just in the test section of the coupon, which would be for p from 1 to 350, in the example of FIG. 5. The maximum value of c(p) or "$c(p)_{max}$" is compared to a threshold, and if it exceeds the threshold, a detection is declared.

Skilled persons will recognize that solving for the c(p) that minimizes η, for each value of p, and then thresholding the largest c(p), is more likely to yield a detection in the instance in which a section of the coupon not only has some intensity (that is, contrast or difference relative to a background noise level, which may be shown as darkness against a white background), but also where the portion tested has a similar shape of intensity profile to Y*(i). As shown in FIG. 4, when the value of p results in the control line being placed directly over itself, c(p) attains its maximum value of "1."

Also, the value of $c(p)_{max}$ is not directly affected by position of p, within the pixel linear array, so that $c(p)_{max}$ may occur at some other location than the value of p that would be expected based on information from the coupon manufacturer. This has a benefit, because coupons sometimes have flaws in the position of the prospective test line, and it is accordingly advantageous to "look" for a test line in a wider area than only where it would be expected based on the intended position. Moreover, when $c(p)_{max}$ is found, the pixel position "p" may yield valuable information concerning the state of the coupon that has been tested.

The procedure determining the values of the parameters "a(p)", "b(p)" and "c(p)" to minimize η are well-known in statistical mathematics. The procedure is performed over the test pixel section to find a value of "c(p)" for each possible pixel starting position "p". When this procedure is performed, it is found that the best-fit value of "c" is given by the following equation:

$$C = K_1 \times S_{iY} + K_2 \times S_Y - K_3 \times S_{YS}$$

The values $K_1$, $K_2$, and $K_3$ are constants that are derived based on the reference signature Y*(i), and are easily calculated by someone knowledgeable in statistical mathematics. The other equation factors are calculated for each sectional pixel array of Y(p) through Y(p+m) to be examined as follows:

$$S_{iY} = \Sigma_{i=p}^{p+m} i \times Y(i) \ldots S_Y = \Sigma_{i=p}^{p+m} Y(i) \ldots S_{YS} = \Sigma_{i=p}^{p+m} Y(i) \times Y^*(i-p)$$

The three summations are easily and quickly calculated and the constants $K_1$, $K_2$, and $K_3$ are only calculated once: After that they may be stored as look-up values for the channel. If the pixel data presented for comparison is the reference pixel array Y*$_i$ itself, the value of "c(p)" will be exactly 1.0 as discussed previously.

As previously discussed, the test line, or pattern, in most cases is essentially identical in shape (that is, in cross-sectional variation in intensity) to the control line, but less intense overall. The value of "c" will have a maximum value when the signal data most closely matches the control line shape Y*(i). This allows identifying the location of each test line center point while the value of "c" represents the relative integral size of the discovered test line as compared to the control line.

This method is favored for several reasons:
  Small variations in the baseline are common due to lighting variations, shadows, and residual color in the coupon substrate. This method automatically estimates and corrects for a non-constant baseline. The value of c(p) is an unbiased best estimate of the baseline-corrected integral value.
  Due to the use of all data points associated with a line, signal-to-noise is improved and a wide dynamic range is realized of as much as 100 to 1. That is, a test line with a value of $c(p)_{max}$ on the order of 0.01 may be detected.
  The value of $c(p)_{max}$ reflects the target substance concentration, which allows development of a calibration curve that quantitatively correlates the targeted material's concentration with the value of $c(p)_{max}$.
  The method allows a quantitative determination that a test line's response is statistically above background noise.

The method provides the lines' peak value location, which is useful in identification of manufacturing or user errors.

While the method can be applied to raw data as well as ratiometric data, the integral value from ratiometric data provides a measure of signal strength that is independent of absolute light intensity or light exposure time as long as the color channels all change proportionately the same when these factors are varied. This is a reasonable assumption for changes in exposure time or temperature, since both the control line and test line will see the same environmental shifts.

In a preferred embodiment, for a multichannel coupon the three constants K1, K2, and K3 are empirically determined for each individual channel by running one or more assays and calculating these least-squares constants for each channel's control line. This may be of particular value if there are differences in channel construction or if assay reagents are significantly different among the channels.

In addition, in a multi-channel coupon the channel control lines may be compared one against another and these relative "c" values stored in the device's memory. During later use, the control lines can be compared to each other to see if any have deviated from the expected relative "c" values. The device may then issue a warning to the user that there may be a problem with one or more channels.

In a preferred embodiment, digital images of the coupon are repeatedly taken over a period of time, starting shortly after addition of the sample and well before the time period suggested by the manufacturer has passed. These images are processed sequentially to determine if a test line has developed. As soon as detection positive result is found, a human perceivable signal is given. Depending on the coupon type, it is possible to gather useful information as early as 1 minute after development has been initiated. Some explosives coupons have a peak color at 2 minutes after application of a test fluid, and noticeably fade after 3 minutes. Accordingly, the time after exposure at which a first digital image is formed may be as little as 10 seconds or even 1 second. The techniques described herein have been shown to reduce the time to detection for bio-coupons to as little as 5 minutes, a third of the time period that the manufacturer recommends waiting, before evaluating an exposed coupon.

Accordingly, in embodiments the taking of digital imagery begins well before the manufacturer's development time has passed. In various embodiments, the taking of digital imagery begins at least 4, 3, 2 and 1 minute prior to the passing of the recommended time to develop, after exposure to said test fluid mixture. Described in different terms, in various embodiments a first digital image is formed no more than 1, 2, 3 and 4 minutes after the coupon channel is exposed to said test fluid mixture.

In a further inventive feature, digital imagery is also repeatedly taken of the control section of each channel, beginning shortly after exposure to a test fluid mixture. This permits early detection of a coupon that has been ineffectively exposed to the test fluid mixture. As soon as ineffective exposure is determined, the test can be terminated and a new test begun, thereby greatly decreasing the time before an accurate reading is determined.

In a further embodiment, the sequence of images are integrated together, to enhance the signal to noise ratio and, in some instances, provide earlier detection than would otherwise be possible. In one variant, time integration is performed on the raw pixels, but in another least squares fitting as described above is applied to the data from each digital image and the multiple results are then integrated over time.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. A method of reading a coupon channel that displays a test pattern in a test section after being exposed to a target substance, said method includes providing a device having a computer readable memory, a digital camera, a logic assembly and a user interface; providing a color-ratio pixel target pattern representation, representative of an exposed and at least partially developed coupon channel control section pattern; placing said color-ratio pixel target pattern into said memory; placing said coupon in said device and exposing said coupon channel to a test fluid mixture; automatically using said digital camera to take a digital image of said coupon channel test section after said exposure, said digital image formed of color pixels, each containing at least two sub-pixels representing the intensity of two different colors; and
   a. wherein the improvement in said method includes for each color pixel forming a color-ratio pixel by forming the ratio of a first one of said two subpixels with the other, and automatically using said logic assembly to compare said color-ratio pixels in said test section as shown in said digital image to said color-ratio pixel target pattern representation to determine if said test section passes a similarity threshold; and in response to a test section passing said similarity threshold, automatically providing a human perceptible indication that the target substance has been detected.

2. The method of claim 1, wherein said coupon channel includes a control section that develops a target pattern after exposure to said test fluid mixture, without regard to the presence of said target substance in said test fluid mixture, and wherein said color-ratio pixel target pattern representation is provided by digital imagery from said digital image of said target pattern in said control section, and further processing in which said color-ratio pixel values are computed and wherein said providing a color-ratio pixel target pattern representation occurs after said exposing said coupon channel to a test fluid mixture.

3. The method of claim 1, wherein said color-ratio pixel target pattern representation is provided by taking a color digital photograph, having color pixels, of a coupon channel that has been exposed to said target substance after a predetermined development time has elapsed since said exposure and computing said color-ratio pixels from said color pixels.

4. The method of claim 1, wherein said threshold is user adjustable and further including the initial step of adjusting said threshold.

5. The method of claim 1, wherein said coupon channel is hosted on a coupon having a single channel only.

6. The method of claim 1, wherein said coupon channel is hosted on a coupon having multiple channels.

* * * * *